United States Patent [19]

Bell et al.

[11] 4,248,084

[45] Feb. 3, 1981

[54] BOMB CALORIMETER

[75] Inventors: Frank H. Bell, Brigham City; Denzel H. Bair, Garland, both of Utah

[73] Assignee: Thiokol Corporation, Newtown, Pa.

[21] Appl. No.: 51,667

[22] Filed: Jun. 25, 1979

[51] Int. Cl.[3] .......................................... G01K 17/00
[52] U.S. Cl. ................................. 73/191; 102/38 R
[58] Field of Search ............................................. 73/191

[56] References Cited

U.S. PATENT DOCUMENTS

| 1,115,238 | 10/1914 | Parr | 73/191 |
| 1,247,998 | 11/1917 | Parr | 73/191 |
| 1,263,763 | 4/1918 | Hasting | 73/191 |
| 3,204,450 | 9/1965 | Von Fuchs | 73/191 X |
| 4,013,419 | 3/1977 | Betzer et al. | 73/191 X |

Primary Examiner—Daniel M. Yasich
Attorney, Agent, or Firm—William R. Wright, Jr.; Thomas W. Brennan; Gerald K. White

[57] ABSTRACT

A bomb calorimeter is presented in which a cartridge type specimen holder is provided in a fitted bomb casing so that a separate pressure seal is no longer required and the ease of making repeated tests is enhanced. The overall efficiency is also improved because of the central location of the specimen holder.

22 Claims, 2 Drawing Figures

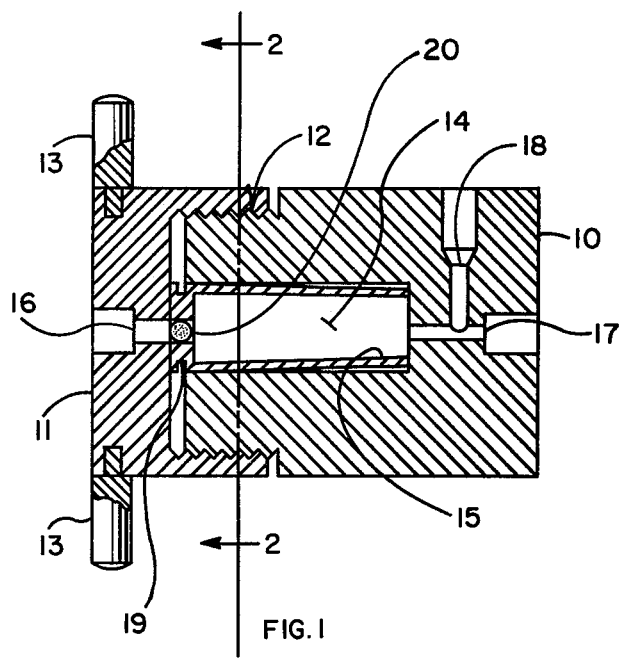
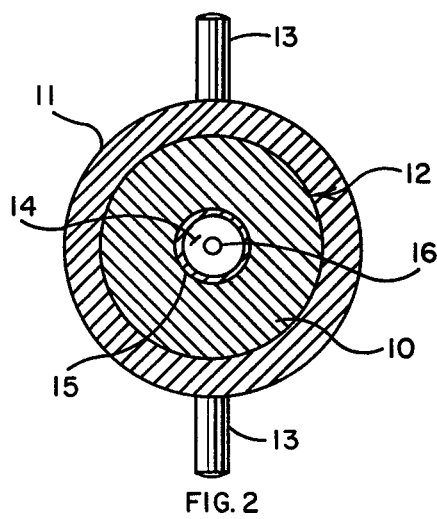

BOMB CALORIMETER

BACKGROUND OF THE INVENTION AND DISCUSSION OF THE PRIOR ART

Bomb calorimeters have long been used in the laboratory for the purpose of performing tests to determine the heat output of a sample of a combustible material and are particularly useful when comparisons must be made between various types or varied compositions of fuels. Such tests are ordinarily performed by burning a small sample of fuel with oxygen inside a small gas-tight enclosure or "bomb" having a combustion chamber which is surrounded by water held in a jacket of the calorimeter. Temperature measurements of the water are taken before, during and after the burning of the sample and are a measure of the heat output of the sample. Repeated tests are made in order to determine the ratings of the various fuels under test and comparisons can then be made so that the correct fuel or composition of fuels can be selected to meet a certain need.

There are, however, certain problems which arise in the performance of such tests which slow down the rate of performance of them and make testing both time-consuming, tedious and expensive, particularly where many repeated tests are to be made. In addition, the accuracy of the tests may be affected because of the problem of making sure each time that a gas tight seal is achieved after the sample has been placed therein. Also, the sample must be carefully placed in the same location in the bomb in order that the heat flow pattern will be the same each time since the temperature measuring equipment will be in the same place for each test. In the present invention, these problems are solved by the provision of a specimen holder for the bomb which has its own seal built into it, which will not leave any residue or char to be removed each time before re-assembly of the bomb, and which always locates the specimen centrally of the bomb without adjustment.

An example of a bomb calorimeter is shown in the McGraw-Hill Encyclopedia of Science and Technology (published in 1960) on page 420 of Volume 2 where a schematic diagram is shown. A written description of calorimetry and types of calorimeters is also included on pages 419 and 420 thereof. From a study of this diagram, it is apparent that the various problems mentioned above are present since no particular provision is made for a seal let alone provision for a quick, clean and simply installed new seal suitable for repeated tests. Furthermore, the specimen holder is not centrally located within the bomb and would likely vary in its location with repeated tests since it is not positively located each time a test is made.

In addition, a discussion of calorimetry and diagrams of some of the early devices used for measurement are included in Volume 4 pages 662 through 669 and Volume 11 page 233 of the Encyclopedia Brittanica both in the edition published in 1969. The diagrams of the mechanisms used do not present the advanced features which are included in the present invention.

OBJECTS OF THE INVENTION

Accordingly, it is an object of the present invention to provide a bomb calorimeter bomb in which the specimen holder is always in substantially the same location for each test.

It is also an object of the present invention to provide a bomb calorimeter bomb wherein the specimen holder is located substantially centrally of the bomb for each test without any need for adjustment.

It is also an object of the present invention to provide a bomb calorimeter bomb wherein repeated tests can be made without delays caused by cleaning off burned or used seals after each test.

It is also an object of the present invention to provide a bomb calorimeter bomb wherein the specimen holder and a seal are integral.

It is also an object of the present invention to provide a bomb calorimeter bomb wherein the specimen holder automatically becomes sealed to the combustion chamber wall of the bomb upon assembly of the bomb.

It is also an object of the present invention to provide a porting system to take transducer measurements and to introduce oxygen to the interior of the bomb combustion chamber wherein only a single through-hole or port which is located on the axis of symmetry of the bomb is needed.

Other objects and advantages of the present invention will become apparent from the detailed description and claims which follows.

THE DRAWINGS

FIG. 1 is a side elevation of the bomb calorimeter in cross section with the specimen holder and the cover cap in place;

FIG. 2 is a transverse cross section of the device taken on section line 2—2 looking in the direction of the cover.

DETAILED DESCRIPTION OF THE INVENTION

In a preferred embodiment of the invention and with particular reference to FIG. 1 of the drawings, a gas-tight enclosure is shown comprising two main separable portions, namely a body 10 and a cover 11 with the cover 11 adapted to be screwed in place on body 10 being coupled thereto by means of screw threads 12. Handles 13 extend outwardly from cover 11 as shown in FIGS. 1 and 2 and are provided to facilitate tightening of cover 11 onto body 10. The body 10 is preferably cylindrical in form so as to provide a symmetrical heat flow pattern from a sample burning in its interior and, for this same reason, a cylindrical bore or combustion chamber 14 is provided in body 10 with its longitudinal central axis coincident with the longitudinal central axis of body 10. An oxygen inlet port 17 is provided in communication with combustion chamber 14 and with a suitable oxygen supply system (not shown) and a pressure transducer connector port 18 is communicably connected into port 17 at substantially a 90 degree angle thereto. This feature permits the bomb chamber to be entered or ported only on the axis of symmetry of body 10 and furthermore, since only a single hole or port is required through the wall of body 10, possible weakening thereof is minimized which would not be the case if more than one hole was provided.

The body 10 and its cover 11 are both made of a suitable metal such as steel and have a thick section to provide more than adequate strength to resist the bursting pressure developed by a specimen burning in chamber 14.

An igniter port 16 is provided on cover 11 and is in communication with an ignition means or igniter 20 of the chamber 14 as shown in FIG. 1.

The specimen holder 15 is a hollow casing which is slightly frusto-conical in form and is so dimensioned that its smaller diameter end (right hand end in FIG. 1) will fit loosely in the bore of chamber 14 while its larger diameter (left hand end in FIG. 1) will be a push fit in the bore thereby providing a seal thereat for sealing and closing chamber 14. The holder 15 is made just long enough so that it will strike the end wall of the bore after the holder 15 has been pushed in place sufficiently to cause "push fit" pressure on the chamber 14 wall but before the external extraction slot or annular groove 19 is covered by the wall as shown in FIG. 1.

The holder 15 is conveniently made from a cartridge for a conventional typical 20 millimeter ammunition round. The casing only is used without any powder or bullet and is reduced in length by cutting it off substantially at a right angle to its longitudinal axis to allow it to fit into chamber 14 and to determine its length so that annular extraction slot or ejection groove 19 will be exposed when the cover 11 is removed but yet an effective seal is realized with the wall of the chamber 14.

The material of which the holder 15 is made is normally of brass since that is the material ordinarily used in cartridges and since it has the qualities which permit it to seal firmly against the wall of the bore at the holders 15's largest diameter end.

OPERATION OF THE INVENTION

A specimen of the material to be tested is carefully weighed and placed inside the specimen holder 15 after which the holder 15 is pushed into chamber 14 in body 10 as far as it can go. The cover 11 is then screwed onto body 10 until it is tight. Handles 13 facilitate this action and make it possible to tighten the cover 11 sufficiently by hand without any need for tools. As this action takes place, the left hand end of the specimen holder 15 is acted upon by the cover 11 to force it tightly into the chamber 14 of body 10 to form a gas-tight seal provided by the peripheral surface at the larger diameter of the holder 15 where it bears against the inner wall of bore or chamber 14 similar to that formed by a cartridge in the breech of a gun.

Oxygen is supplied to the chamber through port 17, an igniter 20 is put in place in port 16 and the pressure transducer is communicably connected to port 18. The whole assembly is then immersed in water in a suitable container (not shown) and which is equipped with a temperature measuring device (not shown).

As the igniter 20 is made to operate, the specimen becomes ignited in the presence of the oxygen and burns producing heat which is conducted through the body 10 and the cover 11 into the water raising its temperature. Measurements are taken of this increase so that the heat produced by the specimen can be evaluated and compared with other specimens as they are tested. The pressure of the gases produced by the burning specimen is relieved by venting it through the pressure transducer system.

After completion of a test, cover 11 is separated from body 10 by unthreading the two portions 10 and 11 exposing extraction slot or groove 19 of holder 15. Holder 15 can then be extracted or ejected from chamber 14 by a prying action against body 10 with a screwdriver blade end or other tool of similar design inserted into slot or groove 19.

Holder 15, once removed can be reloaded with a new test specimen for additional testing. Experience has shown this procedure can be repeated several times before holder 15 becomes worn out, and therefore unserviceable.

As mentioned previously in this specification, the body 10 is cylindrical in form and therefore is symmetrical about its longitudinal axis. Also, chamber 14 is cylindrical and has its longitudinal central axis coincident therewith so that it too is symmetrically located with respect to body 10. This feature is important to the overall test results since the heat of combustion of the specimen being tested is conducted outwardly in a uniform pattern so that the temperature readings taken will also be more uniform even though they are taken at various locations in the calorimeter tank due to the symmetry of the bomb with its constant heat transmission distance to the calorimeter fluid.

While there have been shown and described and pointed out the fundamental novel features of the invention as applied to a preferred embodiment, it will be understood that various omissions and substitutions and changes in the form and details of the device illustrated and in its operation may be made by those skilled in the art, without departing from the spirit of the invention. It is the intention, therefore to be limited only as indicated by the scope of the following claims.

What is claimed is:

1. A bomb for a bomb calorimeter for use in a test for determining the heat output of a combustible material specimen or the like, said bomb being comprised of at least two separable portions including a cover and a body, means on said cover and body for coupling said portions together to form an enclosure, a chamber having at least one open end located in said body, port means in said body communicating with said chamber adapted to admit oxygen supplied thereto into said chamber, ignition means in said bomb including an igniter port for initiating combustion of said specimen, extractable specimen holder means in said chamber including means for sealingly closing said chamber and means on said holder means selectively enabling extraction of said holder means from said chamber when said test is completed.

2. A bomb as set forth in claim 1 in which said chamber has a closed end and said port means is in said closed end.

3. A bomb as set forth in claim 1 in which said chamber in said body is located substantially centrally of said enclosure.

4. A bomb as set forth in claim 1 in which said specimen holder means is open at one end and closed at its other end.

5. A bomb as set forth in claim 4 in which holder means open end is located in said chamber and communicates with said port means.

6. A bomb as set forth in claim 4 in which the ignition means is in the closed end of said holder means.

7. A bomb as set forth in claim 1 in which said specimen holder means has an outer surface which is tapered, said holder means is press-fitted in said chamber on said tapered surface whereby said tapered surface provides said means for sealingly closing said chamber.

8. A bomb as set forth in claim 7 in which the largest portion of said tapered surface of said holder means is located substantially at the open end of said chamber.

9. A bomb as set forth in claim 1 in which the chamber is a central bore located in the body of said enclosure.

10. A bomb as set forth in claim 9 in which said holder means is a tapered cylinder having a closed end and an open end adapted to be inserted in said bore and in length when fully inserted extends from a point externally of said bore open end to the opposite end thereof.

11. A bomb as set forth in claim 1 in which said holder means is a shortened cartridge casing.

12. A bomb as set forth in claim 11 in which said cartridge casing is formed from an ordinary 20mm shell.

13. A bomb as set forth in claim 1 in which said port means is located substantially on the longitudinal central axis of said enclosure.

14. A bomb as set forth in claim 1 further including an additional port means communicably connected to said port means.

15. A bomb as set forth in claim 14 in which said additional port means is provided with pressure and temperature transducer means and pressure relief means for determining the temperature and pressure and the venting of the combustion products in said chamber.

16. A bomb as set forth in claim 1 in which the ignition means is in said holder means.

17. A bomb as set forth in claim 1 further including an igniter port means in said cover portion connected to said ignition means.

18. A bomb as set forth in claim 1 in which said cover portion and said body portion are threadably coupled together.

19. A bomb as set forth in claim 18 in which said cover portion is provided with means for facilitating said coupling together of said cover and body portions.

20. A bomb as set forth in claim 1 in which said means for retracting said holder means from said chamber is a slot located in the outer surface of said closed end of said holder means.

21. A bomb as set forth in claim 1 in which said holder means is a hollow tapered body having a length substantially coextensive with said chamber except for a portion which extends beyond said open end to a point outside of said chamber, said means for extracting said holder means being in said extended portion.

22. A bomb as set forth in claim 1 in said holder means is retained in said enclosure between said body portion and said cover portion when said portions are coupled together.

* * * * *

UNITED STATES PATENT OFFICE
CERTIFICATE OF CORRECTION

Patent No. 4248084  Dated February 3, 1981

Inventor(s) Frank H. Bell and Denzel H. Bair

It is certified that error appears in the above-identified patent and that said Letters Patent are hereby corrected as shown below:

In Column 1, after the Title, insert as the first paragraph of the Specification:

--The Government has rights in this invention pursuant to Contract No. DAAD05-73-C-001 amended by the Department of the Army.--

Signed and Sealed this

Fifteenth Day of December 1981

[SEAL]

Attest:

*Attesting Officer*

GERALD J. MOSSINGHOFF

*Commissioner of Patents and Trademarks*